Feb. 10, 1959 H. C. SWIM Plant Pat. 1,810
ROSE PLANT
Filed April 15, 1958
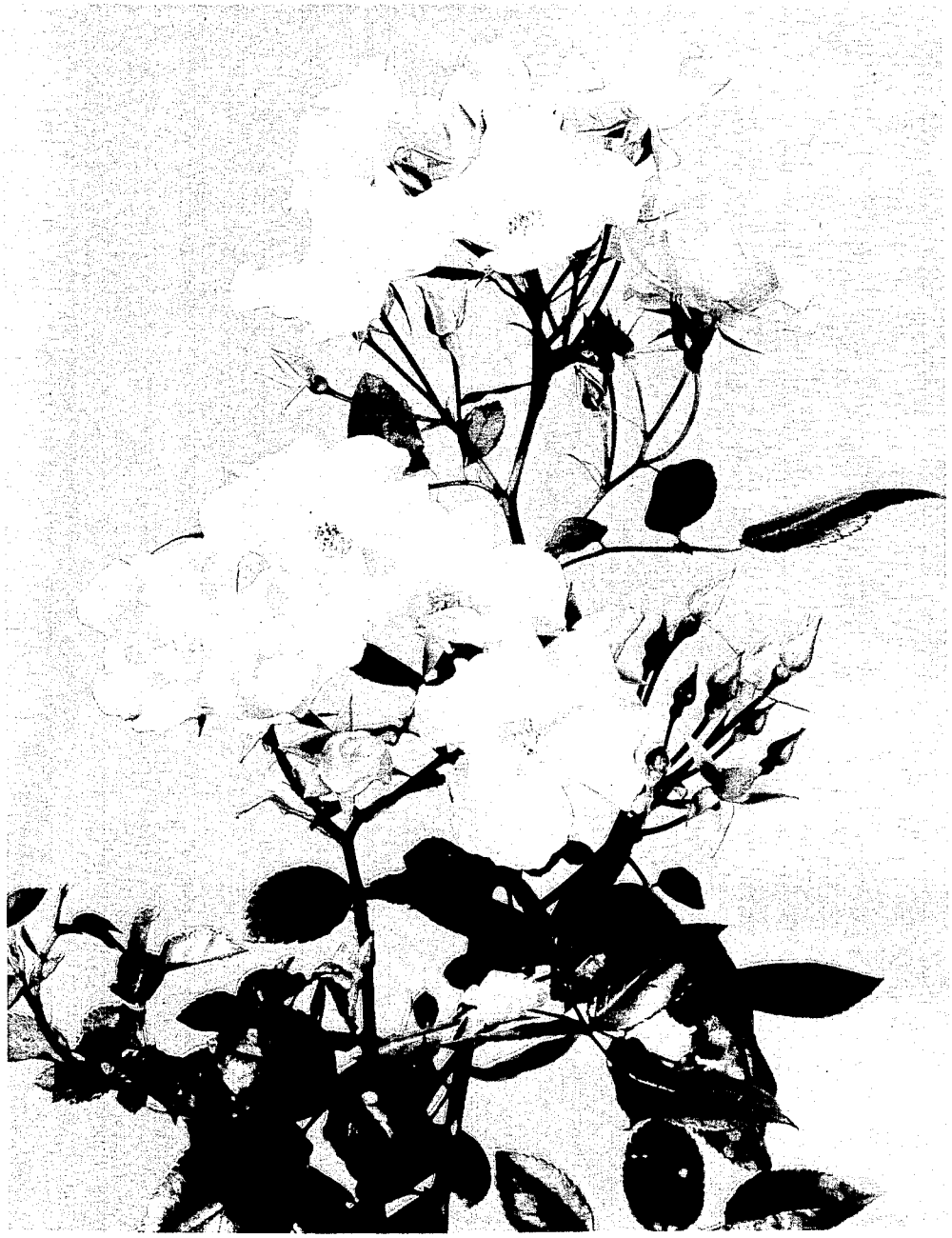
Inventor
H. C. Swim
By Robb & Robb
Attorneys.

United States Patent Office

Plant Pat. 1,810
Patented Feb. 10, 1959

1,810

ROSE PLANT

Herbert C. Swim, Ontario, Calif., assignor to Armstrong Nurseries, Inc., Ontario, Calif., a corporation of California Application April 15, 1958, Serial No. 728,758

1 Claim. (Cl. 47—61)

The present invention relates to a new and distinct variety of rose plant of the polyantha class, which was originated by me by crossing the variety "China Doll" (Plant Patent No. 678) with the variety "Mrs. Dudley Fulton" (Plant Patent No. 122).

The primary objective of this breeding was to produce a semi-dwarf rose which is especially suitable for landscape use. Ancillary to this general objective, it was a further object to create a new rose variety having a plant size intermediate that of the parent varieties, combined with a compact bush habit, attractive and disease-resistant foliage, good floriferousness, a flower size intermediate that of the parent varieties, while at the same time, in proper proportion to the size of the foliage, and an attractive flower color in the range from white to pink or darker.

The foregoing objectives were fully achieved, along with other desirable features, as evidenced by the following unique combination of characteristics which are outstanding in the new variety:

(1) Vigorous, much-branched, semi-dwarf plant of attractive, rounded, bushy and compact habit;

(2) Attractive, glossy, disease-resistant foliage ranging in size from small to medium, and covering the plant well.

(3) Very floriferous and ever-blooming flower habit, with the flowers borne in many clusters ranging from medium to large size, and with the flowers almost completely covering the plant when in peak bloom;

(4) Small, single flowers of attractive ruffled form when fully open; and (5) A distinctive general color tonality of the flowers ranging from white to very pale yellow, shaded or tinged with pink.

In comparison with its seed parent, "China Doll," the new variety is characterized by its larger and more vigorous plant, larger foliage, and the flowers are somewhat larger than those of this parent and are single and near white or very pale yellow in color, with tinges of pink, whereas the flowers of the parent are double and definitely pink.

As compared with its pollen parent, "Mrs. Dudley Fulton," the plant of the new variety is smaller and less vigorous than that of this parent, but has a more bushy and compact habit, and the flowers are smaller and have shadings of pink, whereas the flowers of this parent are white.

From the foregoing, it will be recognized that the new variety is definitely differentiated from its parents, as well as from all other varieties of which I am aware, and asexual reproduction of the new variety by budding, as performed at Ontario, California, shows that the aforesaid characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Robert F. Wilson's Horticultural Colour Chart (hereinafter abbreviated as "Wilson") and Robert Ridgway's Color Standards and Nomenclature (hereinafter abbreviated as "Ridgway"), except where general color terms of ordinary dictionary significance are obvious:

Type: Semi-dwarf; bush; outdoor; seedling; for cut flowers and for garden decoration.
Class: Polyantha.
Breeding: Seedling.
*Seed parent.*—"China Doll."
*Pollen parent.*—"Mrs. Dudley Fulton."
Propagation: Holds its distinguishing characteristics through succeeding propagations by budding.

*Flower*

Locality where grown and observed: Ontario, California.
Flowers borne: Usually many to stem; in irregular rounded to flat clusters; on short stems of normal strength.
Quantity of bloom: Very abundant, outdoors.
Continuity: Nearly continuous during growing season.
Fragrance: From none to slight.
Bud:
*Peduncle.*—Short; slender; erect; usually smooth. Color—near Parrot Green, Plate VI (Ridgway), overlaid with between Mineral Red, Plate XXVII (Ridgway) and Dark Mineral Red, Plate XXVII (Ridgway).
*Before calyx breaks.*—Size—small. Form—medium length; pointed; ovoid.
*As calyx breaks.*—Color—near Empire Yellow, Plate 603/2, page 66 (Wilson), marked or blushed with between Carmine, Plate 21/1, page 21 (Wilson) and Carmine, Plate 21/3, page 21 (Wilson).
*Sepals.*—Inner surface—with fine, woolly tomentum; margins of alternate sepals lined with fine, woolly tomentum; others lined with few, small stipitate glands and short, slender foliaceous appendages. Outer surface—usually smooth.
*As first petal opens.*—Size—very small. Form—medium length; ovoid. Color: Outside—near Empire Yellow, Plate 603/3, page 66 (Wilson), with markings of near Carmine, Plate 21/3, page 21 Wilson), and with small area at base of petal near Empire Yellow, Plate 603/1, page 66 (Wilson); inside—between Primrose Yellow, Plate 601/3, page 65 (Wilson) and Venetian Pink, Plate 420/2, page 125 (Wilson), with small area at base of petal near Empire Yellow, Plate 603/1, page 66 (Wilson).
*Opening.*—Opens up well; is not prevented from opening by cold, hot, wet or dry weather.

Bloom:
*Size (when fully open).*—Small; from 1½ inches to 2 inches.
*Petalage.*—Single; usually 5 petals; arranged regularly.
*Form.*—Cupped at first, but becoming flat to cupped; petals at first being very loosely cupped, with tips reflexed outward, but later becoming somewhat flat at maturity.

Petals:
*Texture.*—Medium thickness. Inside—satiny. Outside—satiny.
*Shape*—Round, with apex flat.

This description of a newly opened flower was made from a rose grown outdoors in the month of November at Ontario, California:

*Color.*—Outside surface—near Empire Yellow, Plate 603/3, page 66 (Wilson), with markings of near Carmine, Plate 21/3, page 21 (Wilson), and with small area at base of petal near Empire Yellow, Plate 603/1, page 66 (Wilson). Inside surface—near Primrose Yellow, Plate 601/3, page 65 (Wilson), shaded with near Venetian Pink, Plate 420/2, page 125 (Wilson), and with small area at base of petal near Empire Yellow, Plate 603/1, page 66 (Wilson).

This description was made from a rose that was open for 3 days outdoors in the month of November at Ontario, California:

*Color.*—Outside surface—between White and Naples Yellow, Plate 403/3, page 121 (Wilson), with shadings of near Rose Pink, Plate 427, page 126 (Wilson), and with small area at base of petal near Primrose Yellow, Plate 601/2, page 65 (Wilson). Inside surface—between White and Naples Yellow, Plate 403/3, page 121 (Wilson), with shadings of near Rose Pink, Plate 427/2, page 126 (Wilson).

*General color effect.*—Newly opened flower—near Empire Yellow, Plate 603/3, page 66 (Wilson), with shadings of near Venetian Pink, Plate 420/2, page 125 (Wilson). 3-days open—between White and Naples Yellow, Plate 403/3, page 121 (Wilson), with shadings of near Rose Pink, Plate 427/3, page 126 (Wilson).

*Behavior.*—Drop off cleanly; not particularly affected by cold, hot, wet or dry weather.

*Flower longevity.*—On bush in garden—from 3 to 5 days in November. Cut roses grown outdoors and kept at living-room temperatures—2 or 3 days in November.

*Reproductive organs*

Stamens: From few to average number; arranged regularly about pistils.

Filaments: Short; from 1 to 5 mm. in length; most with anthers. Color—near Canary Yellow, Plate 2/2, page 2 (Wilson).

Anthers: Small; all open approximately at once. Color: upper side—margins near Saffron Yellow, Plate 7/2, page 7 (Wilson), with remainder near Canary Yellow, Plate 2/2, page 2 (Wilson); under side—margins near Saffron Yellow, Plate 7/2, page 7 (Wilson), with remainder near Canary Yellow, Plate 2/2, page 2 (Wilson).

Pollen: Sparse. Color—near Saffron Yellow, Plate 7/2, page 7 (Wilson).

Pistils: From few to average number; approximately 25 in number.

Styles: Moderately even; short; 3 or 4 mm. in length; thin; bunched. Color—near uranium green, Plate 63/2, page 63 (Wilson).

Stigma: Color—near Uranium Green, Plate 63/3, page 63 (Wilson).

Ovaries: Usually all enclosed in calyx.

Hips: Very short, globular; smooth; walls thin and fleshy. Color (one-half mature)—near Absinthe Green, Plate XXXI (Ridgway), overlaid with near Mikado Brown, Plate XXIX (Ridgway) on side exposed to the sun.

Sepals: Falling soon; short; curled. Color: inside—near Light Grape Green, Plate XLI (Ridgway); outside—near Absinthe Green, Plate XXXI (Ridgway).

Seeds: Very few; from 1 to 4 in number per open-pollinated hip; small.

*Plant*

Foliage:

*Leaves.*—Compound of usually 3 to 7 leaflets; normal abundance; from small to medium size; leathery; glossy.

*Leaflets.*—Shape—oval, usually with apex acute. Base—round. Margin—simply serrate.

*Color.*—Mature: upper surface—between Parrot Green, Plate VI (Ridgway) and Cedar Green, Plate VI (Ridgway), with margins sometimes near Dark Mineral Red, Plate XXVII (Ridgway) until completely mature; under surface—near Biscay Green, Plate XVII (Ridgway). Young: upper surface—between Parrot Green, Plate VI (Ridgway) and Citrine, Plate IV (Ridgway), with margins between Mineral Red, Plate XXVII (Ridgway) and Dark Mineral Red, Plate XXVII (Ridgway); under surface—near Biscay Green, Plate XVII (Ridgway), shaded with near Madder Brown, Plate XIII (Ridgway).

*Rachis (the supporting stem of the compound leaf).*—From light to average size. Upper side—grooved; with few stipitate glands on edges. Under side—moderately smooth; with some small prickles.

*Stipules.*—Short; from narrow to medium width; with short points turning out at an angle of more than 45°.

*Disease resistance.*—Better than average resistance to mildew, as compared with other varieties grown under comparable cultural conditions at Ontario, California.

Growth:

*Habit.*—Semi-dwarf; bushy; upright-spreading; much-branched.

*Growth.*—Vigorous.

*Canes.*—From light to medium caliper.

*Main stems.*—Color—near Citrine Drab, Plate XL (Ridgway). Large prickles—from few to several; from short to medium length; hooked slightly downward; with narrow base of medium length; color—near Army Brown, Plate XL (Ridgway). Small prickles—few; color—near Army Brown, Plate XL (Ridgway). Hairs—none.

*Branches.*—Color—near Rainette Green, Plate XXXI (Ridgway). Large prickles—few; moderately short; hooked slightly downward; with narrow base of medium length; color—near Rood's Brown, Plate XXVIII (Ridgway). Small prickles—very few; color—near Rood's Brown, Plate XXVIII (Ridgway). Hairs—none.

*New shoots.*—Color—near Lime Green, Plate XXXI (Ridgway), overlaid with near Prussian Red, Plate XXVII (Ridgway) on side exposed to the sun. Large prickles—from few to several; short; hooked slightly downward; with narrow base of medium length; color—near Ocher Red, Plate XXVII (Ridgway). Small prickles—few; color—near Ocher Red, Plate XXVII (Ridgway). Hairs—none.

I claim:

A new and distinct variety of rose plant of the polyantha class, substantially as herein shown and described, characterized particularly as to novelty by its unique combination of vigorous, much-branched, semi-dwarf and attractive rounded, bushy and compact plant habits, attractive, glossy, disease-resistant foliage ranging from small to medium size and covering the plant well, very floriferous and ever-blooming flowering habit, with the flowers borne in many clusters of from medium to large size and almost completely covering the plant when in peak bloom, small, single flowers of attractive ruffled form when fully open, and a distinctive general color tonality of the flowers ranging from white to very pale yellow, shaded or tinged with pink.

No references cited.